United States Patent [19]

Richmond et al.

[11] Patent Number: 5,328,701

[45] Date of Patent: Jul. 12, 1994

[54] TISSUE IRRIGATION SOLUTION

[75] Inventors: John E. Richmond, Doylestown, Pa.; Bernard E. McCarey, Atlanta, Ga.

[73] Assignee: Peregrine Surgical Ltd., Doylestown, Pa.

[21] Appl. No.: 943,434

[22] Filed: Sep. 10, 1992

[51] Int. Cl.$^5$ .................. A61K 33/00; A61K 33/10
[52] U.S. Cl. ................................. 424/680; 514/912
[58] Field of Search ..................... 424/680; 514/912

[56] References Cited

U.S. PATENT DOCUMENTS

| | | | |
|---|---|---|---|
| 4,002,758 | 1/1977 | Bigou | 424/263 |
| 4,238,482 | 12/1980 | Peyman et al. | 536/112 |
| 4,414,202 | 11/1983 | Silvetti | 424/DIG. 13 |
| 4,443,432 | 4/1984 | Garabedian et al. | 424/127 |
| 4,550,022 | 10/1985 | Garabedian et al. | 424/606 |
| 4,597,965 | 7/1986 | Holly | 424/81 |
| 4,696,917 | 9/1987 | Lindstrom et al. | 514/54 |
| 4,711,780 | 12/1987 | Fahim | 514/562 |
| 4,713,375 | 12/1987 | Lindstrom et al. | 514/54 |
| 4,725,586 | 2/1988 | Lindstrom et al. | 514/54 |
| 4,778,679 | 10/1988 | Silvetti | 514/60 |
| 4,819,617 | 4/1989 | Goldberg et al. | 514/912 |
| 4,837,021 | 6/1989 | Andermann et al. | 514/912 |
| 4,886,786 | 12/1989 | Lindstrom et al. | 514/54 |
| 4,938,970 | 7/1990 | Hustead et al. | 424/678 |
| 4,952,573 | 8/1990 | LeClerc et al. | 546/164 |
| 4,965,253 | 10/1990 | Goldberg et al. | |
| 4,975,419 | 12/1990 | Newton et al. | 514/54 |
| 4,983,585 | 1/1991 | Pennell et al. | 514/912 |
| 5,013,714 | 5/1991 | Lindstrom et al. | 514/6 |
| 5,022,413 | 6/1991 | Spina, Jr. et al. | 128/898 |
| 5,032,575 | 7/1991 | Neufeld et al. | 514/12 |
| 5,036,046 | 7/1991 | Neufeld et al. | 514/12 |
| 5,051,443 | 9/1991 | Neufeld et al. | 514/420 |
| 5,053,388 | 10/1991 | Gibson et al. | 514/2 |
| 5,116,868 | 5/1992 | Chen et al. | 514/546 |

Primary Examiner—Marianne M. Cintins
Assistant Examiner—Phyllis G. Spivack
Attorney, Agent, or Firm—Watov & Kipnes

[57] ABSTRACT

A tissue irrigation solution containing at least one electrolyte compatible with tissue and a nutrient source including at least one member of the citric acid cycle, deprotinated derivatives and salts thereof which may include a free radical scavenger and/or a wetting agent, said solution being a one-part solution and having a stable shelf-life.

14 Claims, No Drawings

TISSUE IRRIGATION SOLUTION

FIELD OF THE INVENTION

The present invention is generally directed to an irrigation solution for protecting tissues, particularly during surgical procedures of the eye. The irrigation solution contains a balanced amount of compatible electrolytes and at least one compound from the citric acid cycle.

BACKGROUND OF THE INVENTION

Surgical procedures cause damage to tissues and cells from the invasion of surgical instruments, tissue/tissue contact and the intraocular irrigation media. This invasion can result in the destruction of cells and tissues which can lead to various medical complications. Accordingly, the protection of tissues and cells during surgery is of paramount importance, particularly in ophthalmic surgery owing to the sensitivity of the tissue and cells comprising the eye. During intraocular surgery it is often necessary to flush the anterior chamber and/or maintain the fluid volume in the anterior chamber.

In order to prevent damage to the tissues and cells of the eye, it is known to continuously bathe the eye with liquids which approximate the composition of the body fluids. Early tissue irrigation solutions contained sodium, potassium, calcium and chloride ions having an isotonic electrolyte content. These solutions, however, were of limited success because they did not sufficiently prevent swelling and consequential damage to ocular tissues.

There was also developed a number of irrigation solutions which sought to mimic the composition of the aqueous humor of the eye. The first of these solutions was known as Ringer's solution which included sodium lactate in addition to the electrolytes used in the isotonic electrolyte solution.

A further type of tissue irrigation solution is known as a balanced salt solution (BSS) which contains sodium, potassium, calcium and magnesium ions and an acetate-citrate buffer system.

An additional tissue irrigation solution was developed which combined the Ringer's solution with glutathione and sodium bicarbonate. This solution, known as Glutathione Bicarbonate Ringer Solution (GBR), has been employed as a tissue irrigation solution (B. E. McCarey et al., "Functional and Structural Changes In The Corneal Endothelium During In Vitro Perfusion", *Invest. Ophthalmol.*, 12:410–417 [1973]).

More recently, dextrose and sodium hydrogen phosphate have been added to GBR to obtain an enhanced balanced salt solution (commonly called "BSS Plus").

The irrigation solutions described above suffer from a number of disadvantages. Most importantly, such solutions must be prepared at the site of use from two separate mixtures. This is because the bicarbonate and phosphate ions precipitate in the presence of magnesium and calcium ions. In addition, the bicarbonate and the glutathione tend to decompose within the pH range typically associated with irrigation solutions.

It would therefore be desirable to have a tissue irrigation solution that closely approximates the composition of the tissues to which it is applied (e.g. the aqueous humor) and is sufficiently stable so that it can be packaged and used as a one-part solution without mixing as required by two-part GBR solutions.

SUMMARY OF THE INVENTION

The present invention is generally directed to a tissue irrigation solution in which all of the components may be combined well in advance of use so that the final product need not be prepared at the place of surgery. In its broadest sense, the tissue irrigation solution contains electrolytes compatible with the composition of the tissues to which it is applied and a nutrient source comprising at least one member of the citric acid cycle, also known as the Krebs cycle. In a preferred form of the invention, the citric acid cycle component is stable at temperatures which can be used to heat sterilize the composition.

The components of the present irrigation solution are stable and do not form precipitates as in GBR type solutions. Preferred compounds for providing these ions to the irrigation solution are sodium chloride, potassium chloride, calcium chloride, magnesium sulfate and the like. They include customary ions including sodium, potassium, calcium, magnesium, chloride and sulfate ions.

Additional nutrient sources, preferably having a high enough boiling point so that the solution can be heat sterilized, may be employed in the irrigation solution. Pyruvic acid is an example of an additional nutrient source. An organic buffer system, preferably based on a zwitterionic compound such as HEPES (N'-2-hydroxyethyl piperazine-N-ethane sulfonic acid), is used in combination with bicarbonate ions to form a buffer system to eliminate ions which form unwanted precipitates and to reduce the sensitivity of bicarbonate ions to the level of carbon dioxide in solution. In another aspect of the invention, a wetting agent is included in the irrigation solution to reduce surface tension and therefore provide additional protection for the tissues.

DETAILED DESCRIPTION OF THE INVENTION

The irrigation solution of the present invention includes at least one electrolyte compatible with the tissue to which the solution is applied, particularly human tissue such as the aqueous humor of the eye. In its broadest aspect, the irrigation solution also includes a nutrient source comprising at least one member of the citric acid or Krebs cycle, preferably a member of the citric acid cycle having a boiling point high enough to allow heat sterilization such as by autoclaving, e.g. at least 150° C.

The citric acid or Krebs cycle was discovered in 1937. Pyruvic acid, formed in glycolysis is converted to acetyl Co-A. It is then broken down in the Krebs cycle where oxaloacetic acid is constantly regenerated and the resulting energy is captured by coenzymes. The members of the Krebs cycle which may be employed in the irrigation solution of the present invention are citric acid, cis-aconitic acid, isocitric acid, α-ketoglutaric acid, succinic acid, fumaric acid, malic acid and oxaloacetic acid and the deprotinated derivatives and salts thereof and mixtures thereof. Citric acid, α-ketoglutaric acid, succinic acid, fumaric acid, deprotinated derivatives and salts thereof, having a boiling point exceeding 150° C., are preferred.

In addition to the presence of at least one member of the citric acid cycle, the present irrigation solution is void of phosphate ions which tend to precipitate in the presence of calcium as in GBR type solutions. Accordingly, the present invention may be prepared as a one-part solution with a long shelf life.

The buffer system of the present solution preferably includes a zwitterionic compound such as N-2-hydroxyethyl piperazine-N'-ethane sulfonic acid, commonly sold under the trade name HEPES, which is pH adjusted with hydrogen or hydroxyl ions.

The preferred buffer system is one that does not require the addition of carbon dioxide. A zwitterionic compound such as HEPES is stable and exhibits reduced membrane penetration because of its high degree of polarity. In addition, the zwitterionic compound exhibits negligible binding of magnesium and calcium ions and therefore eliminates unwanted precipitates which necessitate the making of a two-part solution.

The osmolality of the solution is desirably isotonic with respect to the tissues to be treated. For corneal cells and general ophthalmic use the osmolality of the solution should be within the range of 270 to 340 mOsm, preferably 300 to 310 mOsm.

The osmotic pressure of the solution is dependent on the number of ions therein. Accordingly, the osmotic pressure can be adjusted within the desired range by adjusting the ion concentration of the irrigation solution. Since the smaller ions (such as sodium, potassium and chloride ions) can rapidly equilibrate across the membranes of the eye tissue, the total osmolality of the irrigation solution is more important than the precise content of the smaller electrolyte ions.

Body fluids must be buffered to protect the pH range for normal metabolic function of the cells. The bicarbonate ion in conjunction with the concentration of carbon dioxide in the body fluids generally determines the pH. The pH of eye tissue is generally in the range of from about 6.5 to 8.5. The irrigation solution of the present invention through its buffer system maintains the pH within this broad range, preferably about 7.4.

The irrigation solution may also contain optional additives including free radical scavengers such as cysteine (oxidized form of cystine), oxidized glutathione, Vitamin E ($\alpha$-tocopherol), mercaptoethanol, ascorbic acid and salts thereof, and 1,4-dithiothreitol.

A hydrophilic surface wetting agent may also be included in the present irrigation solution to reduce surface tension of the air/water interfaces that may come into contact with the corneal endothelium and allow the components of the irrigation solution to fully contact the tissues. Examples of surface wetting agents include albumin and globulin in concentrations ranging from 10 to 100 mg %.

The preferred irrigation solution of the present invention is identified in Table 1.

TABLE 1

| ION | CONCENTRATION (mM) |
|---|---|
| Sodium | 120–160 |
| Potassium | 4–10 |
| Calcium | 0.5–3.0 |
| Magnesium | 0.5–3.0 |
| Chloride | 100–130 |
| Bicarbonate | 20–50 |
| Sulfate | 0.5–3.0 |
| Zwitterionic Compound* | 2–10 |
| Nutrient (including Krebs cycle compound) | 15–30 |
| Free Radical Scavenger | 0.2 to 2.0 |

TABLE 1-continued

| ION | CONCENTRATION (mM) |
|---|---|
| Wetting Agent | 10 mg % to 100 mg % |

*Adjust to pH of at least 7 with sodium hydroxide.

EXAMPLE 1

A particularly preferred irrigation solution of the present invention is set forth in Table 2.

TABLE 2

| ION | CONCENTRATION (mM) |
|---|---|
| Sodium | 149.2 |
| Potassium | 6.3 |
| Calcium | 0.68 |
| Magnesium | 0.76 |
| Chloride | 117.5 |
| Bicarbonate | 39.4 |
| Sulfate | 0.76 |
| Succinic Acid* | 3.8 |
| Cysteine | 1.1 |
| Albumin | 20 mg % |
| HEPES** | 20.9 |

*Succinic acid converts to succinate at a pH of 7.
**Adjust to pH 7.4 1N sodium hydroxide.

The irrigation solution of the present invention has a stable shelf-life and may be used for external ocular irrigation and intraocular irrigation applications. For example, the present irrigation solution can be used to flush the ocular surface to remove debris or to wet the epithelial surface during an examination or surgical procedure. In addition, the irrigation solution may be used for all procedures requiring the flushing or replenishing of the aqueous humor, such as during phacoemulsification.

What is claimed is:

1. A tissue irrigation solution for treating the eye consisting essentially of:

| | |
|---|---|
| sodium | 120–160 mM |
| potassium | 4–10 mM |
| calcium | 0.5–3.0 mM |
| magnesium | 0.5–3.0 mM |
| chloride | 100–130 mM |
| bicarbonate | 20–50 mM |
| sulfate | 0.5–3.0 mM |
| at least one member of the citric acid cycle selected from the group consisting of citric acid, cis-aconitic acid, isocitric acid, $\alpha$-ketoglutaric acid, succinic acid, fumaric acid, malic acid, and oxaloacetic acid, and deprotinated derivatives and salts thereof and mixtures of said members, deprotinated derivatives and salts thereof; and | 2.0–10.0 mM |
| zwitterionic compound | 15–30 mM. |

2. The tissue irrigation solution of claim 1 having an osmolarity of 270 to 340 mOsm.

3. The tissue irrigation solution of claim 1 wherein at least one member of the citric acid cycle has a boiling point exceeding 150° C.

4. The tissue irrigation solution of claim 1 wherein the zwitterionic compound is N-2-hydroxyethyl piperazine-N'ethane sulfonic acid.

5. The tissue irrigation solution for treating the eye consisting essentially of:

| | |
|---|---|
| sodium | 120–160 mM |
| potassium | 4–10 mM |
| calcium | 0.5–3.0 mM |
| magnesium | 0.5–3.0 mM |
| chloride | 100–130 mM |
| bicarbonate | 20–50 mM |
| sulfate | 0.5–3.0 mM |
| at least one member of the citric acid cycle selected from the group consisting of citric acid, cis-aconitic acid, isocitric acid, α-ketoglutaric acid, succinic acid, fumaric acid, malic acid, and oxaloacetic acid, and deprotinated derivatives and salts thereof and mixtures of said members, deprotinated derivatives and salts thereof; | 2.0–10.0 mM |
| zwitterionic compound | 15–30 mM; and |

6. The tissue irrigation solution of claim 5 wherein the effective amount of the wetting agent is from 10 mg % to 100 mg %.

7. The tissue irrigation solution of claim 5 wherein the wetting agent is selected from the group consisting of albumin and globulin.

8. The tissue irrigation solution for treating the eye consisting essentially of:

| | |
|---|---|
| sodium | 120–160 mM |
| potassium | 4–10 mM |
| calcium | 0.5–3.0 mM |
| magnesium | 0.5–3.0 mM |
| chloride | 100–130 mM |
| bicarbonate | 20–50 mM |
| sulfate | 0.5–3.0 mM |
| at least one member of the citric acid cycle selected from the group consisting of citric acid, cis-aconitic acid, isocitric acid, α-ketoglutaric acid, succinic acid, fumaric acid, malic acid, and oxaloacetic acid, and deprotinated derivatives and salts thereof and mixtures of said members, deprotinated derivatives and salts thereof; and | 2.0–10.0 mM |
| zwitterionic compound | 15–30 mM | an effective amount of a wetting agent; and an effective amount of a free radical scavenger.

9. The tissue irrigation solution of claim 8 wherein the effective amount of the wetting agent is from 10 mg % to 100 mg %.

10. The tissue irrigation solution of claim 8 wherein the wetting agent is selected from the group consisting of albumin and globulin.

11. The tissue irrigation solution of claim 8 wherein the effective amount of the free radical scavenger is 0.2 to 2.0 mM.

12. The tissue irrigation solution of claim 9 wherein the effective amount of the free radical scavenger is 0.2 to 2.0 mM.

13. The tissue irrigation solution of claim 8 wherein the free radical scavenger is selected from the group consisting of cysteine, oxidized glutathione, Vitamin E, mercaptoethanol, ascorbic acid and salts thereof, and 1,4-dithiothreitol.

14. A tissue irrigation solution for treating the eye consisting essentially of:

| | |
|---|---|
| sodium | 149.2 mM |
| potassium | 6.3 mM |
| calcium | 0.68 mM |
| magnesium | 0.76 mM |
| chloride | 117.5 mM |
| bicarbonate | 39.4 mM |
| sulfate | 0.76 mM |
| succinic acid | 3.8 mM |
| cysteine | 1.1 mM |
| albumin | 20 mg % |
| HEPES | 20.9 mM |

* * * * *

UNITED STATES PATENT AND TRADEMARK OFFICE
CERTIFICATE OF CORRECTION

PATENT NO. : 5,328,701
DATED : July 12, 1994
INVENTOR(S) : John E. Richmond and Bernard E. McCarey It is certified that error appears in the above-indentified patent and that said Letters Patent is hereby corrected as shown below:

Claim 5, line 1 cancel "The" insert --A--.

Claim 5 after the last line, insert beneath the phrase

"zwitterionic compound" --an effective amount of a wetting agent--.

Claim 8, line 1 cancel "The" insert --A--.

Signed and Sealed this

Sixth Day of December, 1994

Attest:

BRUCE LEHMAN

*Attesting Officer*    *Commissioner of Patents and Trademarks*